United States Patent [19]
Ozaki et al.

[11] Patent Number: 5,954,711
[45] Date of Patent: Sep. 21, 1999

[54] LASER TREATMENT APPARATUS

[75] Inventors: Kenya Ozaki, Miyagi; Yasutaka Sukigara, Aichi; Hirokazu Nakamura, Aichi; Masanori Enomoto, Aichi, all of Japan

[73] Assignee: Nidek Co., Ltd., Japan

[21] Appl. No.: 08/363,924

[22] Filed: Dec. 27, 1994

[30] Foreign Application Priority Data

Dec. 28, 1993 [JP] Japan ................................. 5-352686
Jun. 24, 1994 [JP] Japan ................................. 6-166230

[51] Int. Cl.$^6$ ......................................... A61N 5/06
[52] U.S. Cl. ............................. 606/10; 606/6; 606/13
[58] Field of Search .................... 606/2, 3–6, 10–13, 606/16, 17

[56] References Cited

U.S. PATENT DOCUMENTS

| | | | |
|---|---|---|---|
| 4,520,816 | 6/1985 | Schachar et al. | 606/4 |
| 4,648,400 | 3/1987 | Schneider et al. | 606/5 |
| 5,226,903 | 7/1993 | Mizuno | 606/4 |
| 5,342,351 | 8/1994 | Blaha et al. | 606/4 |

*Primary Examiner*—David M. Shay
*Attorney, Agent, or Firm*—Finnegan, Henderson, Farabow, Garrett & Dunner, L.L.P.

[57] ABSTRACT

A laser treatment apparatus providing a slit-lamp microscope with which an eye of a patient is observed, a box unit which is provided with an optical system to deliver a laser beam inside an observing visual field of the slit-lamp microscope, an attachable device which mounts the box unit on the slit-lamp microscope, and an optical fiber through which a laser beam for ophthalmic treatment is delivered to the box unit, wherein the box unit is provided with a dichroic mirror having characteristics of reflecting the laser beam for treatment to the patient's eye while absorbing a therapeutic surgery laser beam being incident to the dichroic mirror.

13 Claims, 9 Drawing Sheets

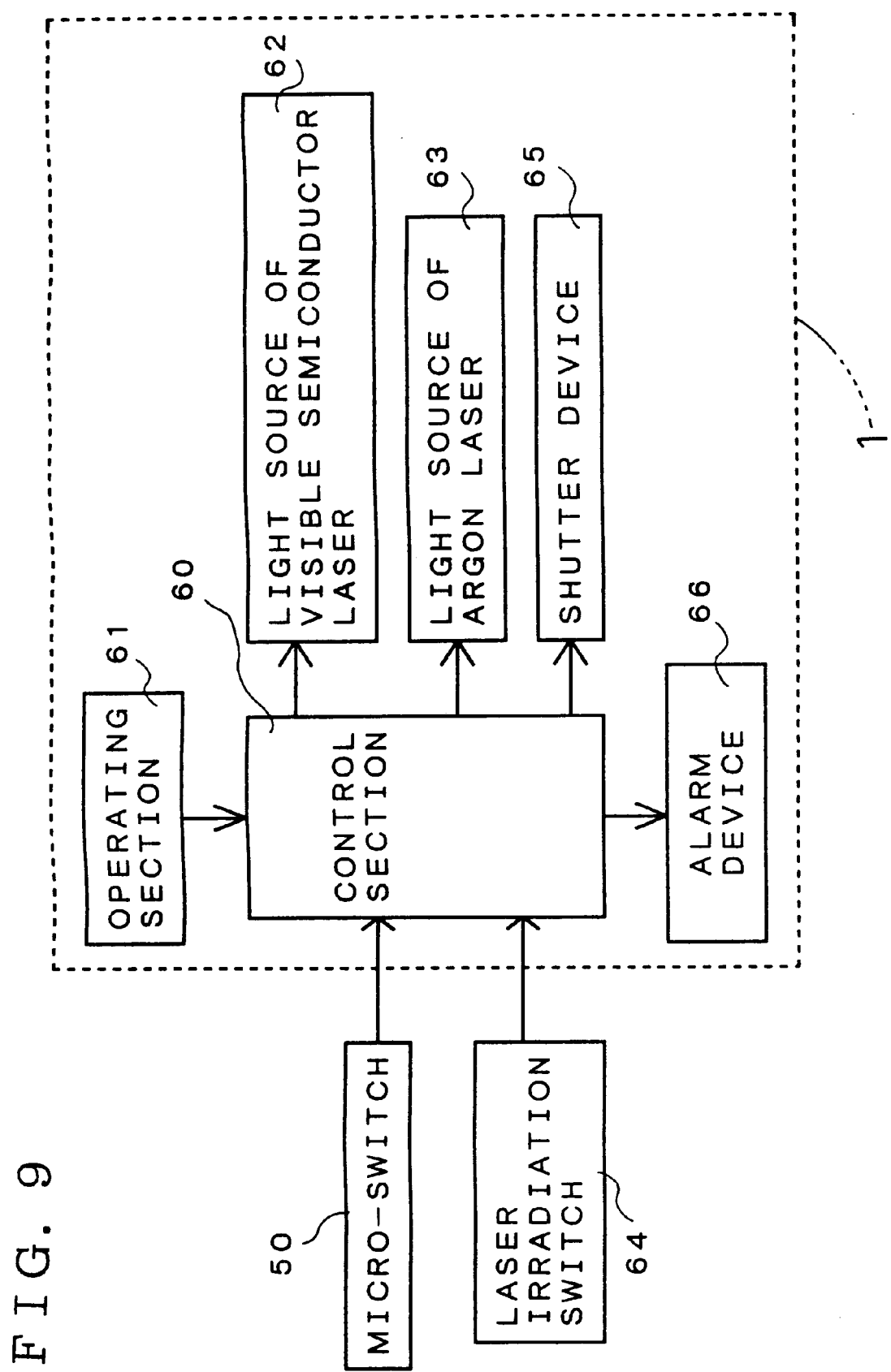

LASER TREATMENT APPARATUS

BACKGROUND OF THE INVENTION

1. Field of the Invention

The present invention relates to a laser treatment apparatus for use in an ophthalmic operation on an eye to be treated by a laser beam, the apparatus using a slit-lamp as an observing optical system, and more particularly to a laser treatment apparatus which comprises a safety mechanism to prevent wrong irradiation of a laser beam.

2. Description of Related Art

Laser treatment apparatus for performing opthalmic operations, in which a laser beam irradiates the affected part of a patient's eye suffering from retinal detachment, for example, then photocoagulating on the irradiated affected part, are known.

Various systems for observing the direction of the transmitted laser beam to the affected part of the eye to be treated, have been proposed. Such proposed observing sytems are selected for use depending on the the condition of the patient, the part of the eye which is affected, and the type of laser to be used. An apparatus using a slit-lamp microscope as an observing optical system is known. This apparatus may allow an attending oculist to stereoscopically observe the patient's eye, and, in particular, it may be used to conduct precise photocoagulation on the affected part of the posterior pole of the eye.

A laser treatment apparatus using a slit-lamp microscope as an observing system is provided with an optical system to transmit or direct a laser beam into an observing optical path of the slit-lamp microscope and a protection device to protect an eye of the oculist from laser beams reflected by lenses and the patient's eye. The protection device has a protection filter for the oculist, which is constructed so as to be located out of the optical path of the observing system to provide sufficient brightness to the oculist during observation and to be moved into the optical path in accordance with trigger signals of laser irradiation.

However, it is difficult to attach reflecting mirrors to direct a laser beam and removably attach a protection filter to a conventional slit-lamp without substantial modification, while there may be no particular difficulty in designing the slit-lamp microscope as a simple purpose device of a laser treatment apparatus.

If the conventional slit-lamp microscope is provided with the reflecting mirrors and a removable protection filter, then a sufficient working distance between the slit-lamp microscope and the patient's eye can not be obtained.

Further, to obtain a sufficient working distance, the protect filter must be fixedly located on the optical path of the slit-lamp microscope. When the protection filter is so fixedly located on the optical path, a part of an observation light beam is eclipsed by the protection filter even when laser treatment operation is not carried out, as a result, the patient's eye can not be observed adequately.

In a slit-lamp microscope having no protection filter, if a switch for laser irradiation is turned on by mistake, a laser beam as projected will be transmitted to the oculist's eye, therefore causing a problem of lack of safety.

SUMMARY OF THE INVENTION

The present invention has been made in view of the above circumstances and has an object to overcome the above problems and to provide a laser treatment apparatus capable of providing a sufficient working distance and a satisfactory observing view without substantially modifying slit-lamp microscopes in the prior art.

Another object of the present invention is providing a laser treatment apparatus provided with a safety mechanism for preventing improper laser irradiation when a laser beam transmitting optical system is not located at a prescribed position on an observation optical path of a slit-lamp microscope.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, a laser treatment apparatus of this invention comprises a slit-lamp microscope with which an eye of a patient is observed; a box unit which is provided with an optical system for transmitting a laser beam inside an observing visual field of the slit-lamp microscope; means for mounting the box unit on the slit-lamp microscope; and an optical fiber for conducting a laser beam for ophthalmic treatment to the box unit, wherein the box unit is provided with a dichroic mirror having characteristics for reflecting the laser beam for treatment to the patient's eye while absorbing a laser beam incident to the dichroic mirror for therapeutic surgery.

In the second aspect of the present invention, a laser treatment apparatus provided with a slit-lamp microscope with which an eye of a patient is observed, comprises an optical member which reflects a laser beam for treatment to the patient's eye and substantially shuts off the laser beam reflected by the eye; a light delivering optical system for delivering the laser beam for treatment into an observing optical path of the slit-lamp microscope; means for mounting the light transmitting optical system on the slit-lamp microscope; means for detecting whether the light transmitting optical system is disposed at a predetermined position on the observing optical path of the slit-lamp microscope; and means for restricting irradiation of the laser beam for treatment in accordance with detected results by the detecting means.

In the third aspect of the present invention, a laser treatment apparatus comprises a slit-lamp microscope with which an eye of a patient is observed; a laser beam generator for generating a laser beam for treatment; a light transmitting system for transmitting the laser beam for treatment generated by the laser beam generator to an observing optical system of the slit-lamp microscope,wherein the light transmitting optical system is provided with an optical member which reflects the laser beam for treatment to the patient's eye while prevents a reflection laser beam of the laser beam incident to the eye from being incident to an eye of an oculist.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings,

FIG. 7 (b) is an enlarged sectional view of a part of FIG. 7 (a);

FIG. 8 (b) is a plane view showing the laser coagulation attachable device of FIG. 8 (a) moved to and located in a holding position; and FIG. 9 is a block diagram of a control system of the apparatus in the present embodiment.

DETAILED DESCRIPTION OF THE PREFERRED EMBODIMENTS

A detailed description of preferred embodiments of a laser treatment apparatus embodying the present invention will now be given referring to the accompanying drawings.

Figure 1:
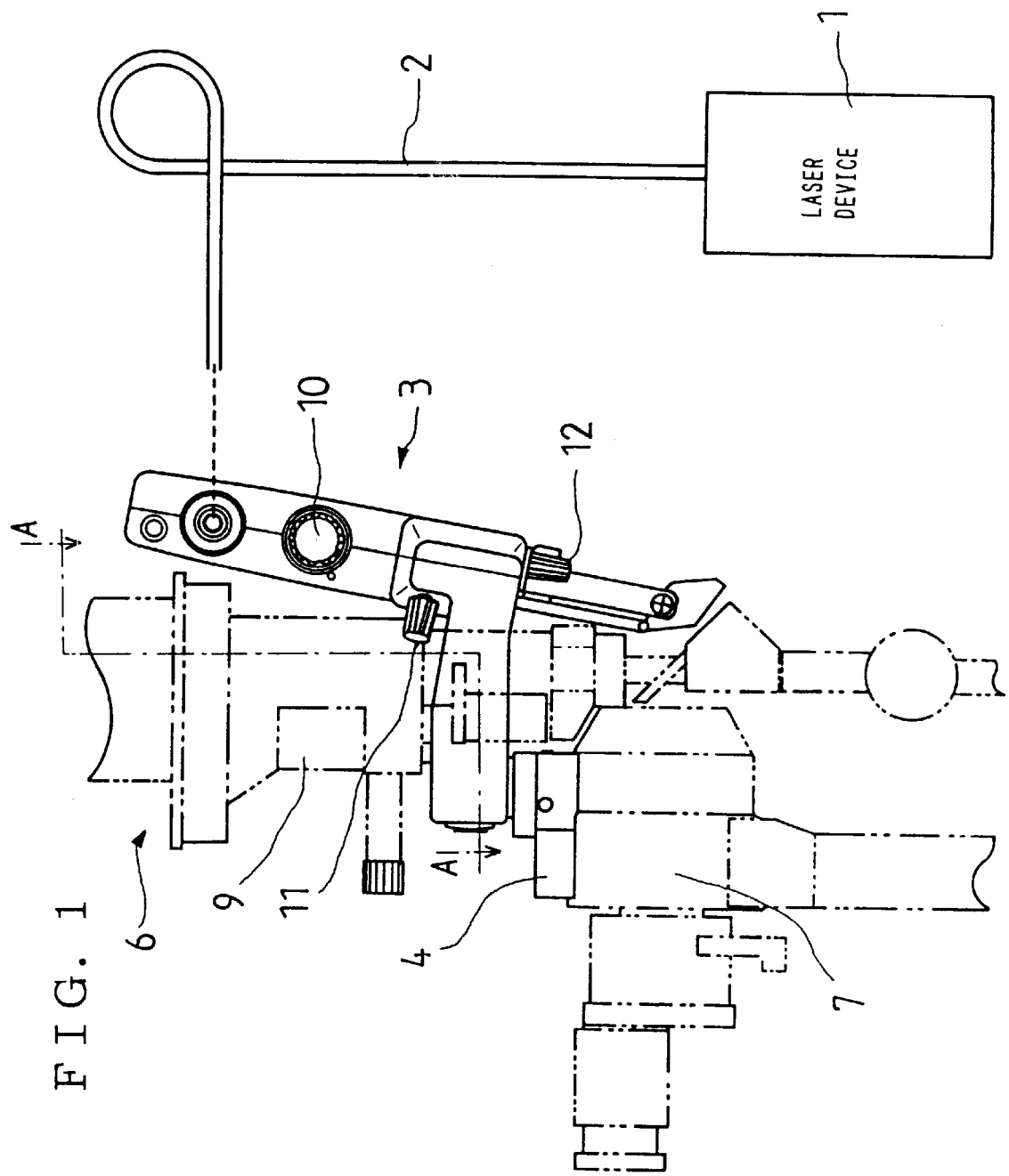
FIG. 1 is a schematic outer side view of a main part of the apparatus of the first embodiment according to the present invention.
Figure 2:
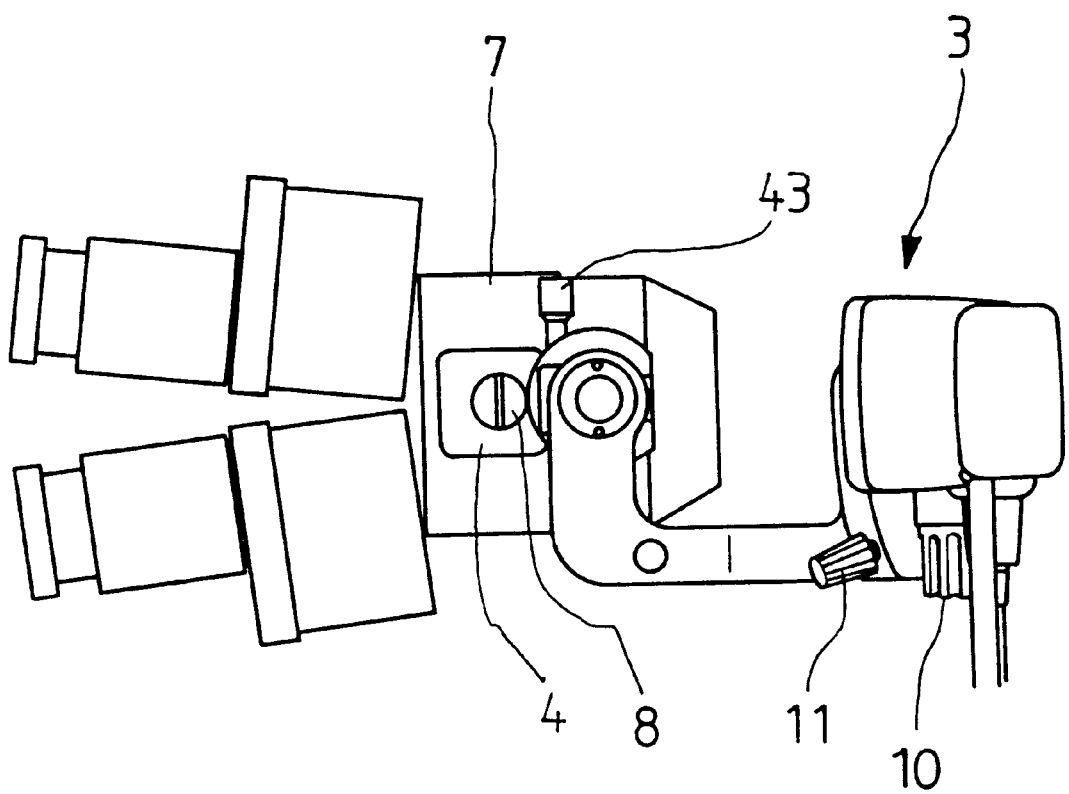
FIG. 2 is a schematic plane view of showing a part of the apparatus of FIG. 1.

FIG. 1 shows an outer side view of a main part of a laser treatment apparatus in the first embodiment and FIG. 2 shows a partial plane view of a slit-lamp microscope and a laser coagulation attachable device mounted on the slit-lamp microscope, which are constructional members of the apparatus of FIG. 1.

As shown in FIG. 1, the laser treatment apparatus in the first embodiment is provided mainly with a laser device 1 for generating laser beams, a fiber cable 2, a laser coagulation attachable device 3 and a slit-lamp microscope 6.

More specifically, the laser device 1 has internally an argon laser for a therapeutic light and a visible semiconductor laser for an aiming light. An argon laser beam and a visible semiconductor laser beam are made coaxial in the laser device 1 for entry into a fiber cable 2.

Figure 3:
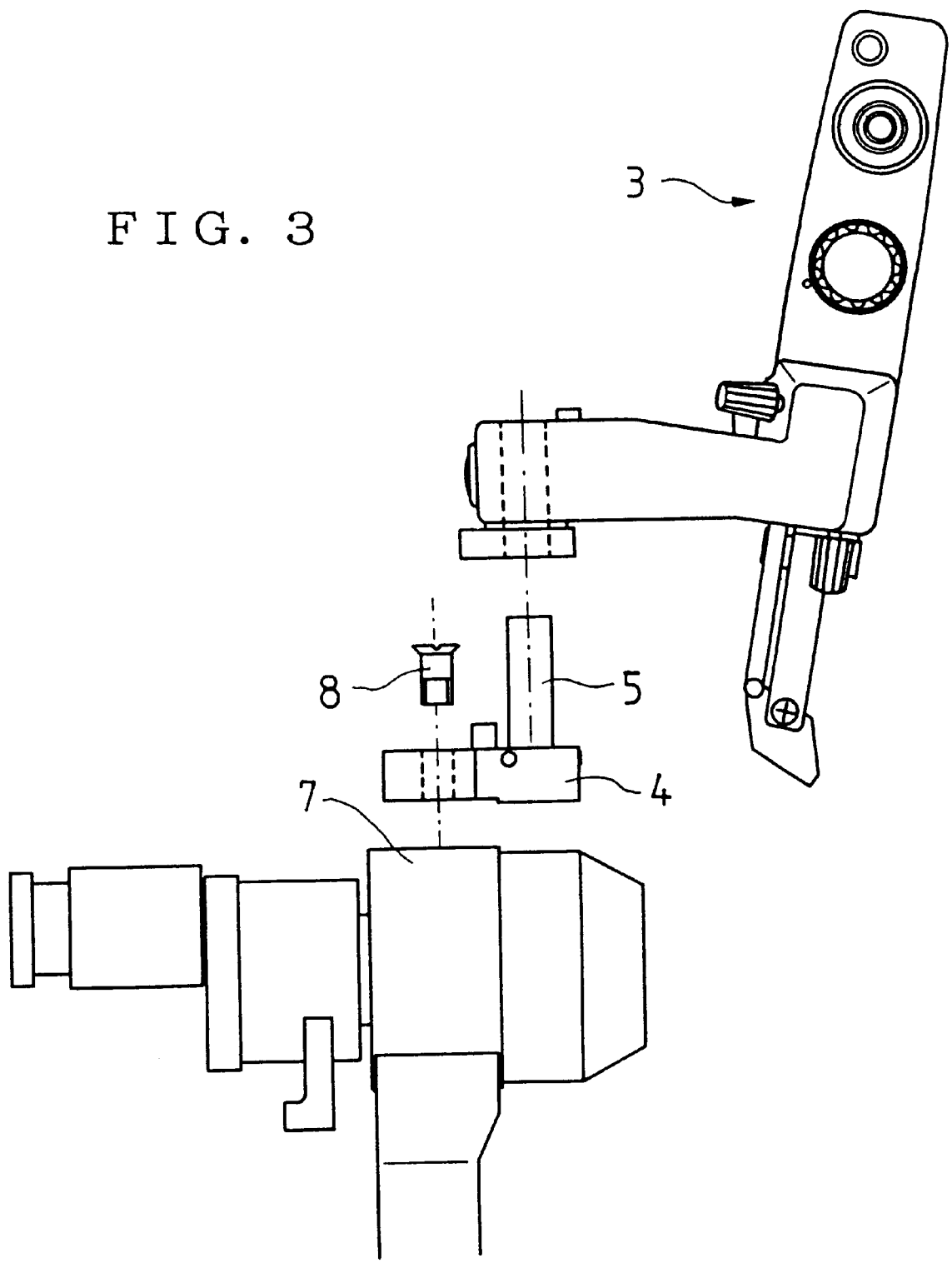
FIG. 3 is a side view of showing a situation of mounting a laser coagulation attachable device on a slit-lamp microscope.
Figure 4:
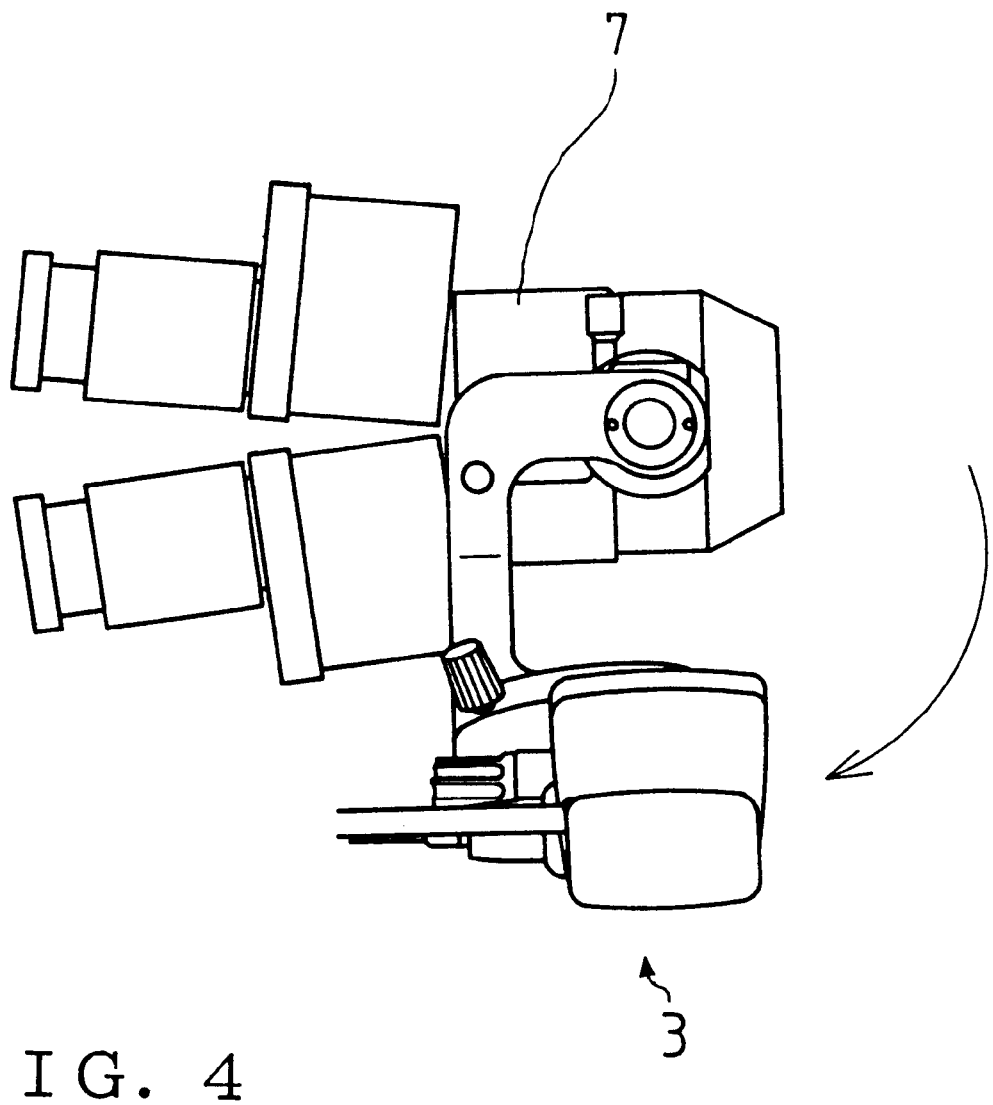
FIG. 4 is a schematic plane view of showing a situation of the laser coagulation attachable device moved to and located in a holding position.

The laser coagulation attachable device 3, whereby an optical system to enable ophthalmic treatment by a laser beam is added to a slit-lamp microscope, is mounted on the slit-lamp microscope 6 through a holder 4. The laser coagulation attachable device 3, as shown in FIG. 3, is rotatably attached to an attaching shaft 5 of the holder 4, while the holder 4 is fixed on an upper portion of a microscope section 7 of the slit-lamp microscope 6 with a screw 8. The laser coagulation attachable device 3 is able to freely move in the direction indicated by a curved arrow shown in FIG. 4 to a holding position when laser coagulating operation is not carried out, thereby to be displaced from an observation optical path of the slit-lamp microscope 6.

The laser coagulation attachable device 3 is provided with a spot size knob 10 to adjust the spot size of a laser beam to be projected on the eye 26, a vertical adjusting knob 11 to adjust a coagulating point by a laser beam in a vertical direction and a horizontal adjusting knob 12 to adjust the coagulating point by a laser beam in a horizontal direction.

Figure 5:
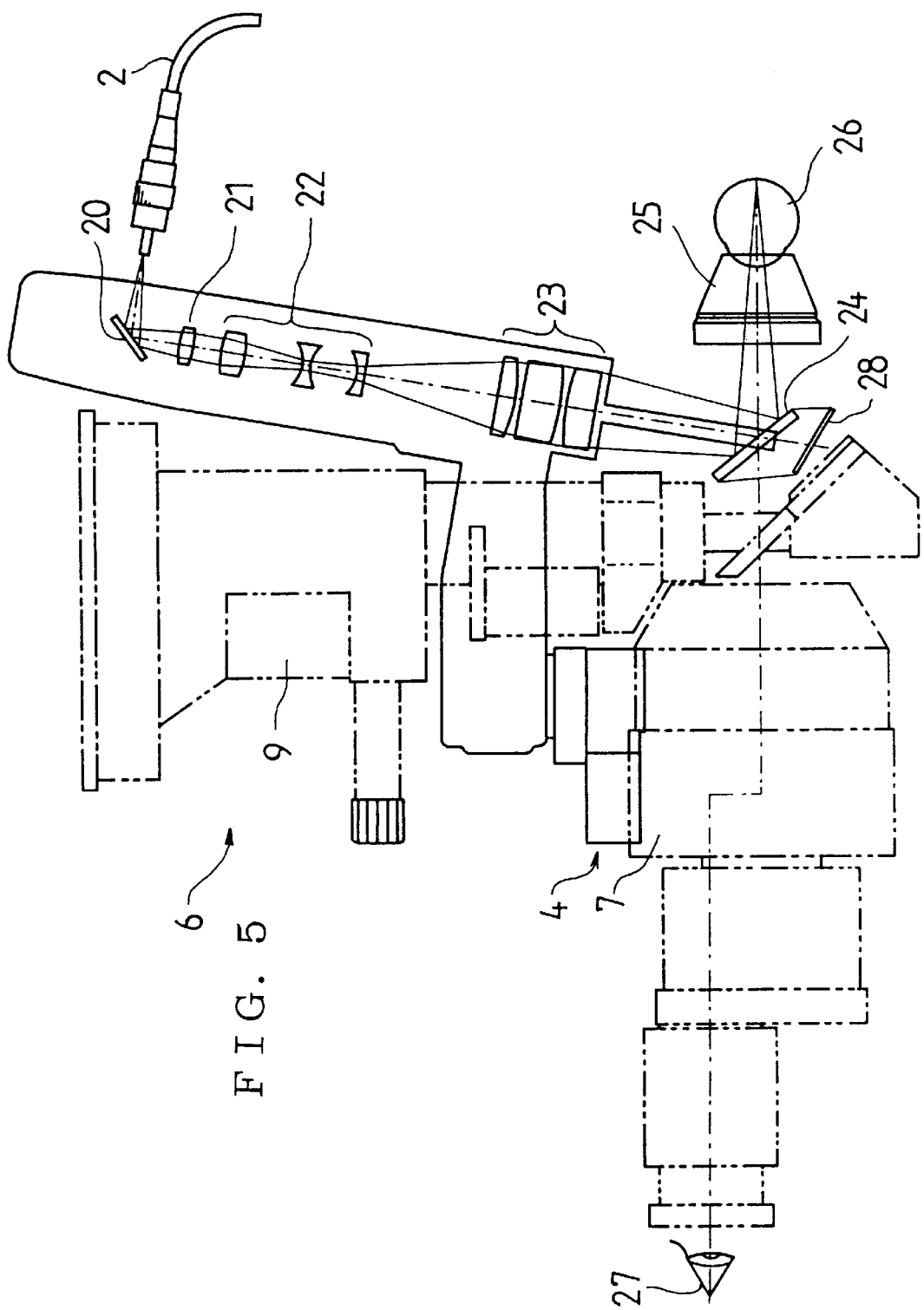
FIG. 5 is a schematic diagram showing an arrangement of the optical system of the laser coagulation attachable device.

Next, the optical system of the laser coagulation attachable device 3 will be explained, an optical arrangement of which is schematically illustrated in FIG. 5.

The optical system of the laser coagulation attachable device 3 is provided with a mirror 20 to reflect a laser beam emitted from the optical fiber 2, a collimator lens 21 through which the laser beam is collimated, a group of zoom lenses 22, a group of objective lenses 23 and a dichroic mirror 24. The group of zoom lenses 22 are movable together with the spot size knob 10 for changing the laser beam spot size that is projected on the fundus of the eye.

Figure 6:
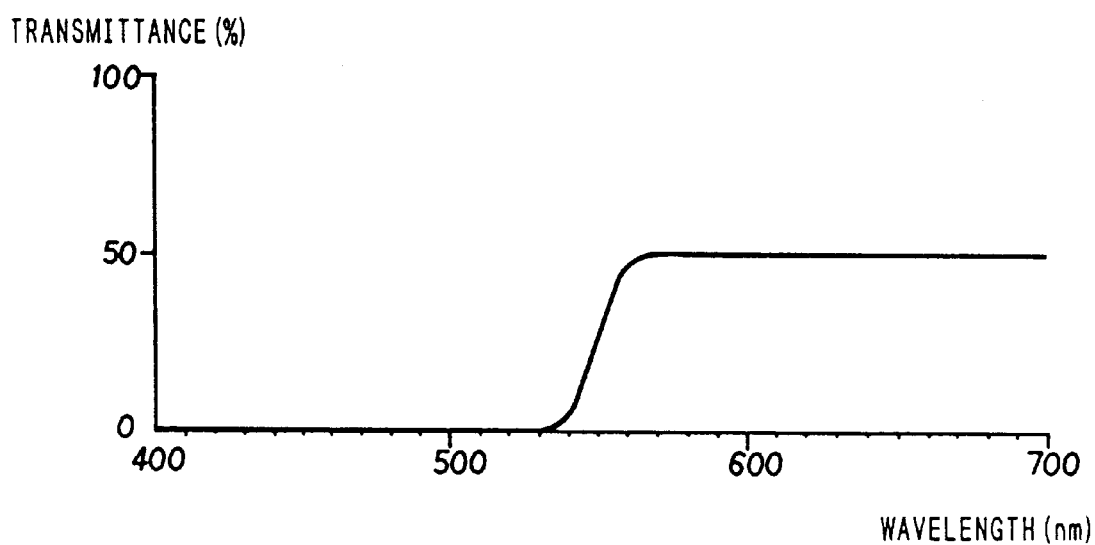
FIG. 6 is a graph showing spectral characteristics of a dichroic mirror 24.

The dichroic mirror 24 functions as a reflecting mirror to reflect the laser beam passed through the objective lenses 23 toward the patient's eye as well as a functioning as a protection filter to protect an oculist's eye from an argon laser beam being reflected by the patient's eye. The dichroic, mirror 24 is supplied with a dichroic mirror coat on the surface thereof. The optical characteristics of the mirror coat itself is reflecting 95% or more of a laser beam having a wavelength of 530 nm or less, which is the wavelength area of an argon laser beam, while transmitting about 60% of a visible light beam having a wavelength of 560 nm or more which includes the wavelength area (650 nm) of a visible semiconductor laser beam. For materials of the dichroic mirror 24, an orange colored sharp cut filter which can absorb an argon laser beam is used in the present embodiment. Thus, the dichroic mirror 24 in the present embodiment as above constructed has a spectral characteristics shown in FIG. 6.

A visible semiconductor laser beam is reflected by the surface of the dichroic mirror 24 and applied to the patient's eye 26 through a contact lens 25. The laser beam is then reflected dispersively on the fundus of the patient's eye 26 and transmitted through the dichroic mirror 24, thus the oculist's eye 27 can look at an aiming light of the visible semiconductor laser beam through an observing optical system of the microscope section 7. A part of the argon laser beam projected on the patient's eye 26 is also reflected by the fundus of the eye 26 and so on, then transmits through the coated surface of the dichroic mirror 24 while it is absorbed in the dichroic mirror 24 due to the mirror material itself, thus not reaching to the oculist's eye 27.

Numeral 28 is an attenuator which will absorb an argon laser beam transmitted through the dichroic mirror 24 and also illumination light of the slit-lamp illumination system 9, which is reflected partially by the dichroic mirror 24.

Setting the operation of the laser coagulation attachable device and coagulating operation therewith will be separately described in conjunction with the apparatus of the first embodiment as above constructed.

Setting Operation of Laser Coagulation Attachable Device

The laser coagulation attachable device 3 is mounted on the slit-lamp microscope 6 with the holder 4 and the screw 8 so as to be rotatable about the attaching shaft 5 and to position the dichroic mirror 24 on the observing optical path of the slit-lamp microscope 6. The spot size knob 10, the vertical adjustment knob 11 and the horizontal adjustment knob 12 are respectively turned so that the location of the aiming light beam is adjusted relative to an illumination light beam.

Coagulating Operation

The head of the patient is held on a head support (not illustrated in figure) of the slit-lamp microscope 6 and then positioned between the apparatus and patient's eye 26 which is performed through a determined operation so that the fundus of the eye 26 may be observed through the microscope section 7 by the oculist. After such positioning, coagulating output power of the laser beam, coagulating time and the like are selected by various switches provided in the laser device 1, and the coagulating size of the laser beam is also determined by turning the spot size knob 10 of the laser coagulation attachable device 3.

Then, the aiming light beam is adjusted to the affected part of the eye 26, and depression of a foot switch (not shown) allows the argon laser beam to irradiate the affected part.

According to the first embodiment, it is possible to use conventional slit-lamp microscopes for the laser treatment apparatus while retaining enough working distance and fine observing vision, without complex modifications.

The second embodiment of the present invention will next be described.

A coagulation attachable device 3 which has an optical system constructed similar to that in the first embodiment is rotatably mounted on a slit-lamp microscope 6. The attachable device 3 is provided with a dichroic mirror detecting system to detect whether a dichroic mirror 24 is positioned on the observing optical path of the slit-lamp microscope 6.

Figure 7B:
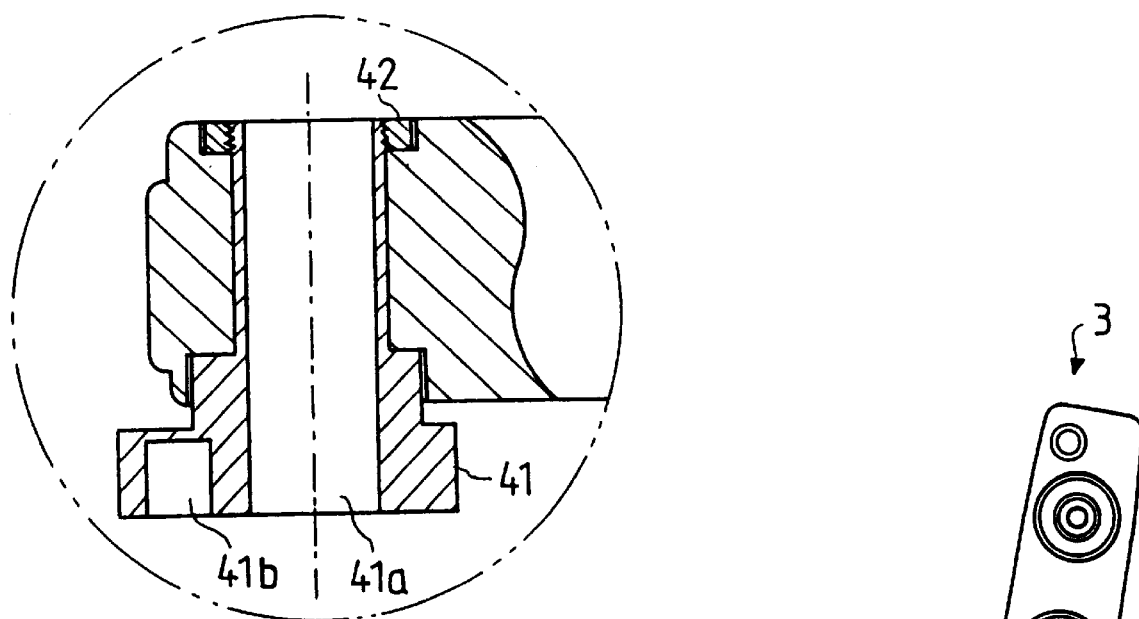
FIG. 7 (a) is an exploded view of showing the mounting mechanism of the laser coagulation attachable device on the slit-lamp microscope according to second embodiment of the present invention.
Figure 7A:
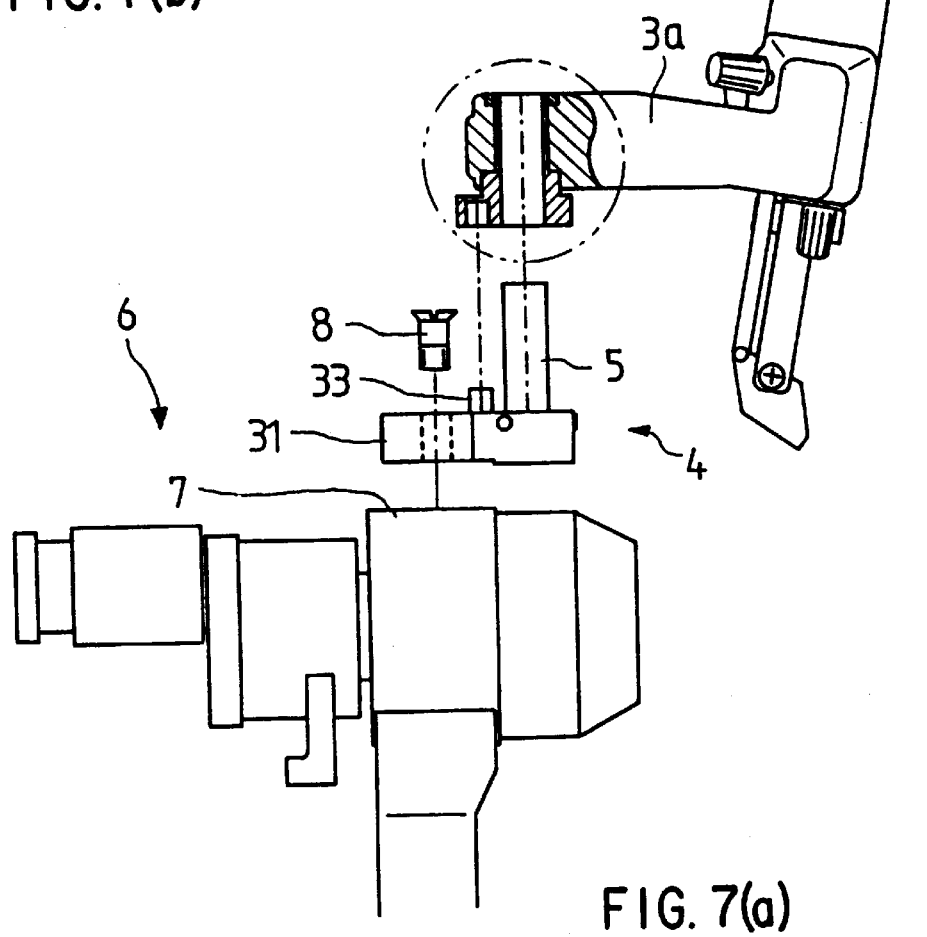

FIGS. 7 (a) and 7 (b) are an exploded side view with a sectional view of a part, which shows the mounting mechanism of the laser coagulation attachable device 3 on the slit-lamp microscope 6. As shown in FIG. 7 (a) and FIG. 7 (b), a holder 4 to mount the laser coagulation attachable device 3 on the slit-lamp microscope 6 is comprised of a mounting base 31, an attaching shaft 5 inserted in the mounting base 31 and a pin 33 inserted in the mounting base 31. The holder 4 is installed fixedly on the top portion of the microscope section 7 of the slit-lamp microscope 6 with the screw 8.

The laser coagulation attachable device 3 has an arm member 3a at which the attachable device 3 is assembled with the slit-lamp microscope 6. Numeral 41 is a rotary base rotatably installed in the arm member 3a with a nut 42, which has a shaft hole 41a in which the shaft 5 is inserted and a pin hole 41b in which the pin 33 is inserted. The shaft 5 and the pin 33 of the holder 4 are inserted in the shaft hole 41a and the pin hole 41b of the rotary base 41, respectively. The rotary base 41 is positioned relative to the holder 4 and is fixed thereto with a fixing knob 43 (shown in FIG. 2).

A click mechanism (not shown) is further provided between the rotary base 41 and the arm member 3a to restrict the rotation of the arm member 3a of the laser coagulation attachable device 3. In a state where the laser coagulation attachable device 3 is mounted on the slit-lamp microscope 6, the laser coagulation attachable device 3 will when fixed at a position where the dichroic mirror 24 (shown in FIG. 5) of the attachable device 3 is located on the observation optical path of the slit-lamp microscope 6 and at the holding position (shown in FIG. 4).

Figure 8:
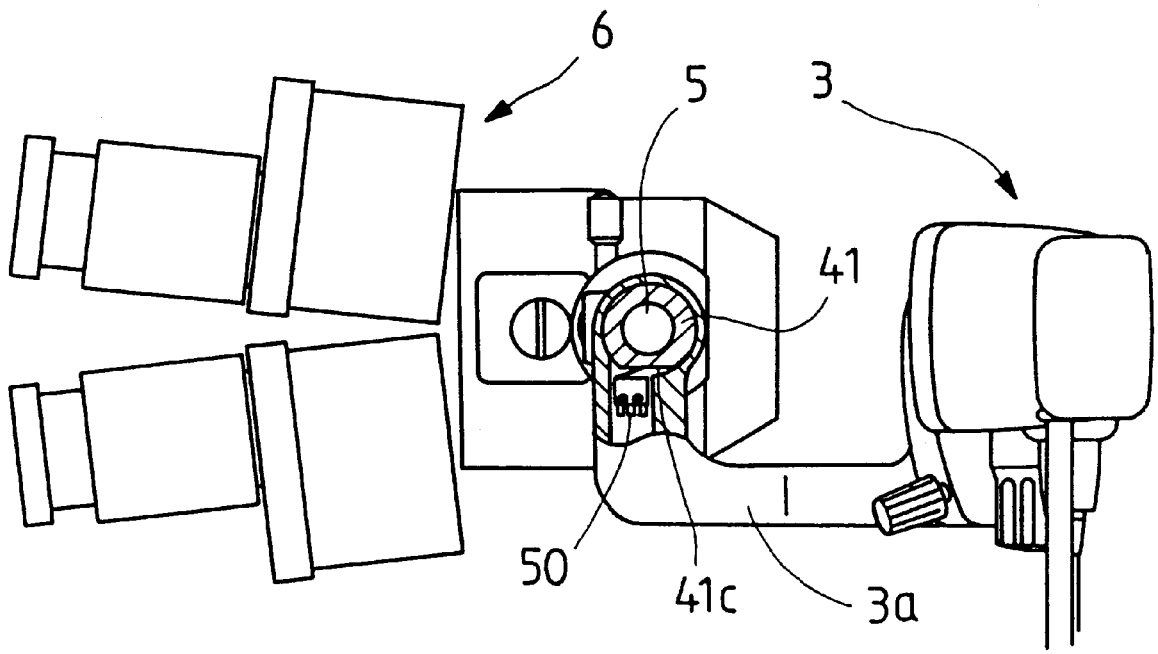
FIG 8 (a) is a sectional view taken on line A—A in FIG. 1.
Figure 8:
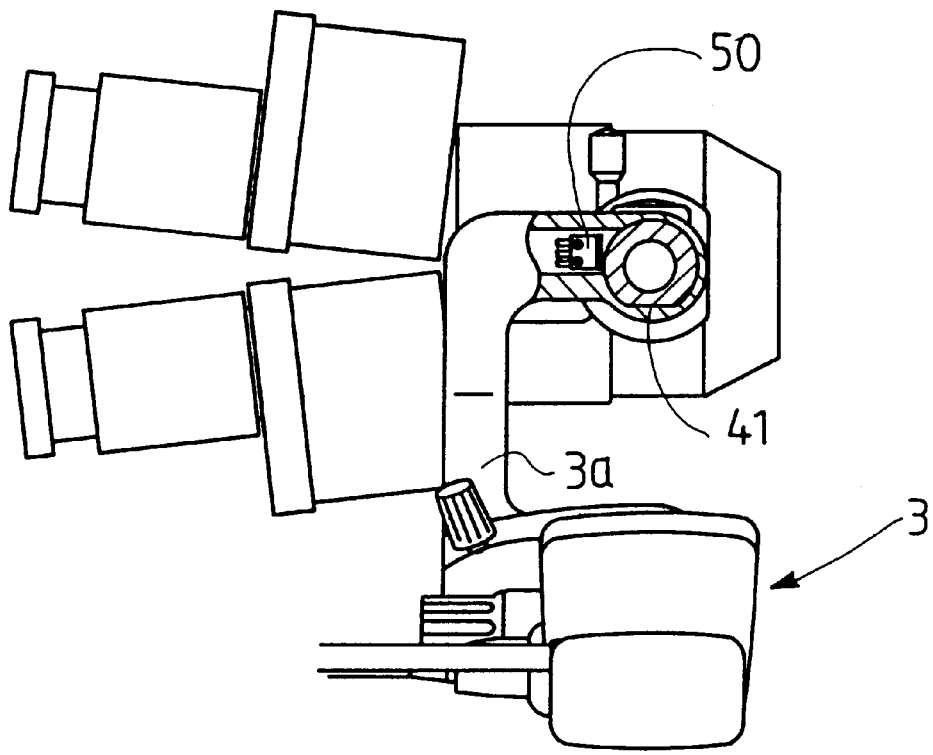

Referring to FIGS. 8 (a) and (b) which are plane views with a partial section taken along line A—A of FIG. 1, the dichroic mirror detecting system of the laser coagulation attachable device 3 will be described below.

The rotary base 41 is provided with a chamfer portion 41c on its peripheral surface at a position having a predetermined relation to the pin hole 41b. Numeral 50 is a microswitch which is fixedly installed in the arm member 3a so as to face the chamfer portion 41c in the laser beam irradiating state shown in FIG. 8 (a), that is to say, in a clicked state of the laser coagulation attachable device 3, at a position where the dichroic mirror 24 is located on the observation optical path of the slit-lamp microscope 6. When the laser coagulation attachable device 3 is turned from the position of FIG. 8 (a) to the holding position of FIG. 8 (b), a contact of the microswitch 50 comes in contact with a peripheral surface, except the chamfer surface of the rotary base 41, thus transmitting electricity. Based on this transmission of electricity, it will be detected that the dichroic mirror 24 deviated from the observation optical path of the slit-lamp microscope 6.

Operation of the dichroic mirror detecting system constructed above in the second embodiment will be described, referring to the control system of FIG. 9.

When a laser coagulation operation is conducted, the laser coagulation attachable device 3 is turned and so located that the dichroic mirror 24 is disposed on the observation optical path of the slit-lamp microscope 6. With the laser coagulation attachable device 3 in such location, the microswitch 50 is facing the chamfer surface 41c, thus shutting off transmission of electricity, so that laser irradiating operation cannot be possible.

Necessary preparations for a coagulating operation are conducted, which include determination of coagulating conditions and the like with various switches located in an operating section 61. After such preparations, the aiming light beam emitted from a light source 62 of visible semiconductor laser is adjusted to aim at affected part of the patient's eye. When a laser irradiation switch 64 is depressed, then a trigger signal 60 is transmitted to the control section 60. The control section 60, which received the signal controls a light source 63 of argon laser to emit an argon laser beam. The argon laser beam emitted from the light source 63 is projected through the optical fiber 2 and the optical system of the laser coagulation attachable device 3 onto the patient's eye to coagulate the affected part of the eye.

When the laser coagulating operation is not being carried out, the attachable device 3 is turned to the holding position and, accordingly, the dichroic mirror 24 is moved out of the observation optical path of the slit-lamp microscope 6. When the dichroic mirror 24 deviates from the observation optical path, the microswitch 50 turns ON and a signal thereof is input to the control section 60. Upon receiving the signal of the microswitch 50, the control section 60 controls a shutter device 65 to shut off the optical path along which the laser beam passes.

In this state, even if the laser irradiation switch 64 is depressed by mistake and as a result laser beams are emitted from the light source 63 of argon laser and the light source 62 of visible semiconductor laser, those laser beams are not transmitted to the laser coagulation attachable device 3. Therefore, dangerous laser irradiation may be prevented.

If the laser irradiation switch 64 is depressed when the microswitch 50 is ON, the control section 60 operates an alarm device 66, such as a buzzer, for example, to inform the oculist that an improper operation is being conducted.

In the second embodiment described above, the microswitch 50 is used as a detecting device. While various kinds of detecting devices, such as a photoelectric switch, can be used, the detecting device may also stop the output power of a laser beam to prevent improper laser irradiation.

Further, according to the second embodiment, whether the laser transmitting optical system additionally provided in the slit-lamp microscope is located at a predetermined position can be automatically detected, and the laser beam is not transmitted to the patient's eye when the laser transmitting optical system is disposed out of the predetermined position.

Consequently, the danger of improper laser irradiation of the patient's eye can be avoided.

The foregoing description of the preferred embodiments of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A laser treatment apparatus comprising:

a slit-lamp microscope having a visual field for observing an eye of a patient;

a box unit containing an optical system for transmitting a laser beam inside the observing visual field of said slit-lamp microscope;

means for mounting said box unit on the slit-lamp microscope; and an optical fiber connected to said box unit for conducting a generated laser beam for both aiming and ophthalmic treatment to said box unit, wherein said optical system includes a dichroic mirror positioned in an observing optical path of the slit-lamp microscope, said dichroic mirror being constructed of a material which absorbs light having a wavelength of the laser beam for treatment, and a mirror surface including a dichroic coat film for reflecting the greater portion of the generated laser beam for opthalmic treatment and for partially reflecting and partially transmitting the laser beam for aiming.

2. A laser treatment apparatus according to claim 1, wherein said laser beam for treatment is a visible laser beam having a first wavelength and the laser beam for aiming light being a visible laser beam having a second wavelength different from that of the laser beam for treatment.

3. A laser treatment apparatus according to claim 1, wherein said box unit mounting means includes means for movably mounting said box unit to removably position the dichroic mirror in the observing visual field.

4. A laser treatment apparatus comprising:

a slit-lamp microscope having an observing optical system for observing an eye of a patient;

a laser transmitting device for transmitting the treatment laser beam on an observing optical path of said slit-lamp microscope, including a dichroic mirror reflecting a treatment laser beam to the patient's eye and substantially shutting off the treatment laser beam reflected by the eye;

a changing device for changing coagulation spot size, mounted on said slit-lamp microscope;

a shifting device for shifting said transmitting device from a coagulation position to a non-coagulation position; and an optical fiber connecting said laser device and said laser transmitting device, through which the treatment laser beam and an aiming laser beam emitted from the laser device are transmitted to the observing optical system of the slit-lamp microscope.

5. A laser treatment apparatus according to claim 4, wherein said treatment laser beam is an argon laser beam and said aiming laser beam is a visible laser beam having the wavelength which is different from and longer than the wavelength of the argon laser beam;

said optical member being constructed of mirror material having sharp cut filter characteristics which absorb the argon laser beam, said optical member having an incident surface on which is applied a dichroic coat filter which reflects light having a wavelength of the argon laser beam while allowing an amount corresponding to one half of the laser beams to tramsmit therethrough.

6. A laser treatment apparatus according to claim 4, further comprising detecting means for detecting whether said optical member is located on the observing optical path of the slit-lamp microscope, wherein the optical path along which the treatment laser beam passes is shut off when it is judged that the optical member is not located on the observing optical path of the slit-lamp microscope based on detected results of the optical member detecting means.

7. A laser treatment apparatus according to claim 6, wherein said optical member detecting means is a microswitch which is turned ON/OFF according to the shifting of the laser transmitting device relative to to said slit-lamp microscope.

8. A laser treatment apparatus according to claim 7, further comprising alarm means for audibly indicating an improper operation when irradiating the treatment laser beam while said microswitch is ON.

9. A laser treatment apparatus having a slit-lamp microscope for observing an eye of a patient, comprising:

a light transmitting optical system for transmitting a laser beam for treatment into an observing optical path of said slit-lamp microscope, said optical system having an optical member for reflecting the laser beam for treatment to the patient's eye and for substantially shutting off the laser beam for treatment reflected by the eye;

means for mounting said light transmitting optical system on said slit-lamp microscope;

detecting means for detecting whether said light transmitting optical system is disposed at a predetermined position on the observing optical path of said slit-lamp microscope; and means for restricting irradiation of the laser beam for treatment in accordance with detected results by said detecting means.

10. A laser treatment apparatus according to claim 9, wherein said detecting means includes a microswitch for detecting whether said mounting means is located at a predetermined position.

11. A laser treatment apparatus according to claim 9, wherein said irradiation restricting means includes a shutter device for shutting off the laser beam so that the laser beam is not transmitted to said light transmitting optical system when it is judged that said light transmitting optical system is not located at a predetermined position on the observing optical path of the slit-lamp microscope based on the detected results by said detecting means.

12. A laser treatment apparatus comprising:

a slit-lamp microscope having an observing optical system for observing an eye of a patient;

a laser beam generator for generating a laser beam for treatment;

a light transmitting optical system connected to the laser beam generator for transmitting the laser beam for treatment to the observing optical system of the slit-lamp microscope, said light transmitting optical system including an optical member which reflects the laser beam for treatment to the patient's eye while preventing a reflection of the laser beam incident to the eye of the patient from being incident to an eye of one viewing the observing optical system of the microscope; and detecting means for detecting whether said optical member is located on a path of the observing optical system of the slit-lamp microscope, the optical path of the treatment laser beam being shut off when it is judged that the optical member is not located on the observing optical path of the slit-lamp microscope, in accordance with signals from the optical member detecting means, said optical member detecting means includes a microswitch which is turned ON/OFF according to the rotation of a laser coagulation member relative to said slit-lamp microscope.

13. A laser treatment apparatus according to claim 12, further comprising alarm means for audibly indicating improper operation when irradiating the laser beam for treatment while said microswitch is ON.

* * * * *